United States Patent [19]

Antonik

[11] 4,080,265

[45] Mar. 21, 1978

[54] METHOD FOR THE DETERMINATION OF CREATIVE PHOSPHOKINASE ENZYME

[76] Inventor: Alan S. Antonik, 599 Exmoor Rd., Elk Grove Village, Ill. 60007

[21] Appl. No.: 722,749

[22] Filed: Sep. 13, 1976

Related U.S. Application Data

[62] Division of Ser. No. 493,874, Aug. 2, 1974, Pat. No. 4,001,088.

[51] Int. Cl.² .............................................. G01N 31/14
[52] U.S. Cl. .............................................. 195/103.5 R
[58] Field of Search ................................ 195/103.5 R

[56] References Cited

U.S. PATENT DOCUMENTS 3,838,012   9/1974   Higgens et al. ............... 195/103.5 R

OTHER PUBLICATIONS

Bergmeyer's "Methods of Enzymatic Analysis", vol. 1 (1974) Academic Press, Inc., N.Y., pp. 165-171.
Strehler et al., Arch. Biochem. Biophysics, 40 (1952) pp. 28-41.

*Primary Examiner*—Lionel M. Shapiro
*Assistant Examiner*—C. A. Fan
*Attorney, Agent, or Firm*—Michael G. Berkman

[57] ABSTRACT

A method for the detection and the quantitative determination of the enzyme creatine phosphokinase (CPK), an agent present in abnormal concentrational levels in serum in many cases of mental disorders and neuromuscular disorders, and significant in the diagnosis of myocardial infarction. The component such as a blood-impregnated carrier substance, obviating the need for separatory procedures (i.e., separating the serum from the blood cells) and special handling (i.e. freezing, freeze drying, etc.) to preserve the sample. The mechanism of the laboratory determination is that adenosine diphosphate (ADP) reacts with creatine phosphate in the presence of creatine phosphokinase and magnesium ions to produce adenosine triphosphate (ATP) plus creatine. The ATP, in turn, reacts with the luciferin and luciferase of the firefly lantern system to produce light (bioluminescence), the intensity of which is proportional to the concentration of CPK initially present. There is provided a test reagent system for carrying out the method of the invention.

9 Claims, No Drawings

METHOD FOR THE DETERMINATION OF CREATIVE PHOSPHOKINASE ENZYME

This application is a divisional of copending application Ser. No. 493,874 filed Aug. 2, 1974 now U.S. Pat. No. 4,001,088.

BACKGROUND OF THE INVENTION

This invention relates to the detection and quantification of serum enzymes in living organisms. The term, serum enzyme, as used herein is meant to include those enzymes occurring normally in the serum, but whose concentration will depend upon or be affected by some pathological condition in the organism, as well as those enzymes not detected in the serum of a normal organism but whose concentration increases under pathological conditions. More particularly, the invention relates to the detection and quantification of the serum enzyme Creatine Kinase (EC 2.7.32 International Union of Biochemistry), commonly known as Creatine Phosphokinase or CPK (referred to as CPK hereinafter). The invention teaches the detection of this enzyme in dried samples contained in a porous carries such as filter paper.

The sample is conveniently obtained from any fluid derived from an organic source such as blood, plasma, serum spinal fluid, organ extracts, tissue fluid, eye tears, body secretions, tissue cultures etc. Studies in the inventor's laboratory and by others have shown the substrate-carried dried sample to be stable for at least one month under normal ambient conditions.

CPK determination is extremely valuable in the detection of neuromuscular disorders (Munsat et al., *Journal of the American Medical Association*, 226-13, Page 1536, Dec. 2, 1973). The measurement of CPK is also of significant value in the diagnosis of myocardial infarction. There is also growing evidence of abnormal levels of CPK present in many cases of mental disorders. Munsat has further shown that abnormally high CPK levels are present in many carriers of Duchenne Muscular Dystrophy (DMD) and tend to be higher in infancy and adolescence.

Detection of preclinical cases of neuromuscular disorders will facilitate a program of early treatment which can result in prolonged mobility. (Demos, Early Diagnosis and Treatment of Rapidly Developing Duchenne DeBologne-type Myopathy (Type DDB 1); *Am. Jour. Phys. Med.* 50-7. Page 271,1971). Demos has demonstrated that CPK is already present in very high amounts in newborn victims of Duchenne Muscular Dystrophy. Duchenne Muscular Dystrophy occurs in a frequency of about 1 in 3500 male births with a similar ratio for carriers (females). *Jour. Hum. Gen.* 11-4, page 360, December, 1959). It also appears that the disease has a mutation rate of about 35%. The method and reagents described herein have been shown to be capable of detecting Duchenne muscular dystrophy preclinically and have also been shown to be capable of detecting the CPK elevations associated with carriers of this disease.

The methods and reagents of the invention are also useful in detecting abnormal levels of CPK in hamsters and pigs. In the 14:6 strain of the Golden Syrian Hamster, this method is extremely valuable as these are cardio-myopathic animals. As such, a non-destructive CPK test (and this is the first such test developed) is invaluable for monitoring the effectiveness of treatment of these animals for cardio and muscular disease using various chemical compounds. In pigs, CPK has been shown to be elevated to significant levels in animals affected by Porcine Stress Syndrom, a disease which causes poor quality pork and substantial losses of pigs due to death in shipment to market.

SUMMARY OF THE INVENTION

Applicant is believed to be the first to have discovered a practical technique for demonstrating CPK activity, or any other serum enzyme, from an ambient-air-dried state. Erythrocytic enzymes such as glucose-6-phosphate dehydrogenase have been determined from dried blood cells but, previously, serum enzymes have required freeze drying of the serum for long-term stability. Of all the currently popularly used serum enzymes, CPK has had a known history of instability and vulnerability to physical conditions (Dalal, F.R. et al. *Clin, Chem.* 18 No. 4. 1972). In accordance with the practice of the present invention, it is now possible to assay CPK as well as other serum enzymes from an air dried state using appropriate methods.

The method of the invention is based on the principal that CPK in the presence of creatine phosphate and adenosine diphosphate (ADP) [(inosine diphosphate (IDP) cytidine diphosphate (CDP), Uridine disphosphate (UDP) and Guanosine disphosphate (GDP) may replace ADP, in decreasing activity] will produce ATP and creatine (See Reaction A below, in the reverse direction). The mechanism is indicated schematically in reversible equilibria diagrammed in Reaction A and Reaction B, below:

REACTION A:

Magnesium is required and the reaction is greatly enhanced by a sulfhydryl group. Other ions may be substituted for magnesium, such ions including manganese, Mn++. The ATP then reacts with the luciferin and luciferase (Reaction B) of the firefly system or in the firefly extract to produce light. The intensity of the light is proportional to the concentration of CPK in the initial reaction system.

REACTION B:

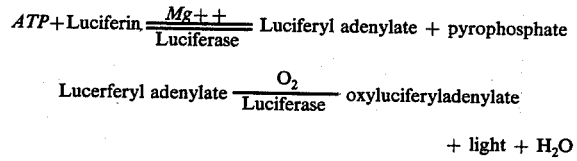

$$+ \text{ light } + H_2O$$

After a short incubation period, the light intensity is measured by means of a photmeter or equivalent instrument, the greater the original concentration of CPK Present, the greater being the production of light.

Bioluminescent reactions of the general type herein relied upon, between andenosine triphosphate ATP and firefly lantern extract are known and have been utilized in the prior art. Such a light emission phenomenon is described in Chappelle U.S. Pat. Nos. 3,575,811 and 3,575,812 which disclose methods for the measurement of ATP in tissue cultures as a technique for detecting the presence of cancerous cells and/or the presence or absence of a virus in a host cell. Chappelle points out that cancerous cells cause lesser light emission than do normal cells (U.S. Pat. No. 3,575,811) and that the ATP content of virus-containing cells is different from the content of ATP in normal cells (U.S. Pat. No. 3,575,812). However, the Chappelle methods are carried out using conventional tissue cultures and involve laboraty techniques, reagents and reactions which differ materially and significantly from those of the present invention. However, the disclosures of the Chappele patents are hereby incorporated herein by reference to the extent they are not inconsistent herewith.

In accordance with the practice of the method of the invention meaningful increases in the concentration of a serum enzyme are readily detected in each of a series of pathological conditions. Typical data indicative of metabolic malfunction in organisms are set forth in the following table for types of mental and neuromuscular disorders which are readily detectable using the techniques of the present invention. In the tabular presentation, the "Disorder" appears in the first column. The second column gives the concentration of CPK in International Units, 50 units being the usual upper limit for a normal human. The relative light units (using an Aminco Chem-Glow Photometer) are shown in the third column, 18 units being about the normal upper limit for a normal human.

and adjusted with NaOH to a pH of 7.4. The pH may vary within a range from about 6.8 to 7.8.

A chelating agent such as ethylenedinitrilo tetraacetic acid (EDTA) at a concentration of about 0.001 M may be used, but is not necessary. The solution (firefly powder, buffer, water and chelating agent) is then centrifuged at 10,000 g for 15 minutes. The speed and time may vary and other separation methods may be used.

Alternative methods for preparing the luciferase-luciferin solution include the following:

1. Use of crystallized luciferase as described by Green and McElroy (Green, A. A. and McElroy, W. D., *Biochem. Biophys. Acta.*, 20,170 (1956).
2. Use of a synthetic luciferin which is available commercially.
3. Use of partially purified luciferin-luciferase solutions prepared by various means such as column chromatography.

A 100 ml buffer solution is prepared using the same procedure as in the above primary extraction. To this solution magnesium ions are added in the form of magnesium acetate, although other organic and inorganic magnesium salts may also be used. The optimum con-

| | TYPICAL LIGHT UNIT READINGS ANTONIK CPK SCREEN | |
|---|---|---|
| Disorder | Reference Method CPK International Units (Rosalki Method) e.g. 50-Upper limit of normal human | Relative Eight Units (Aminco Chem-Glow Photometer) |
| 1. Duchenne Muscular Dystrophy (preclinical) | 4000 | 1860 |
| 2. Duchenne Muscular Dystrophy (initial clinical stages) | 3200 | 1500 |
| 3. Duchenne Muscular Dystrophy (medium stages | 2000 | 1200 |
| 4. DMD (advanced stages) | 400 | 300 |
| 5. Carrier DMD | 100 | 32 |
| 6. Limb-Girdle Dystrophy | 180 | 36 |
| 7. Facio-Scapulo Humeral | 120 | 33 |
| 8. Schizophrenia | 180 | 36 |
| 9. Myocardial Infarction | 400 | 56 |
| 10. Myositis | 3000 | 1450 |
| 11. Porcine Stress Syndrome | 3000 | 1450 |
| 12. Cardio Myopathic Golden Syrian Hamster 14:6 strain | 2800 | 1400 |
| 13. Normal Human | 25 | 12 |
| 14. Normal Pig | 100 | 25 |
| 15. Normal hamster | 12 | 8 |

DETAILED DESCRIPTION OF METHOD

10± 2 grams of freeze-dried firefly lanterns (Freeze-dried firefly lanterns are available commercially), are used for every 1000 ml of stock reagent and 3000 ml of working reagent. The firefly lanterns are ground to a fine powder with a mortar and pestle or other grinding apparatus. An "acetone powder" may also be used. (Such a powder is prepared by washing the firefly lantern powder with acetone, filtering and drying.) The material is then extracted with 1000 ml (1 liter) of a 0.1 M morpholinopropane sulfonic acis (MOPS) buffering agent adjusted to a pH 7.3 with NaOH (sodium hydroxide). The concentration of the buffer may vary by at least from 0.01 to 0.5 M and a variety of other buffers may also be used, such as hydroxymethyl aminomethane and potassium arsenate. In fact, water may be used centration for Mg++ is 0.02 M but the range may extend from 0.002 M to 0.1 M. Chloride and phosphate ions are avoided as these have an inhibitory effect on the overall reaction.

To the above solution is added a sulfhydryl compound such as dithiothreitol, (DIT) dithioerythritol or other such compounds such as glutathione, at a concentration of from about 0.1 to 8 mM, with 1 mM preferred. The sulfhydryl compound serves to activate the CPK as well as to stabilize the luciferase. This buffer solution is added to the primary extraction and the resulting solution (luciferin-luciferase extract, buffer, magnesium ions, and sulphydryl compound) is the stock solution and can be freeze dried in appropriate amounts. The resulting product is referred to as Reagent I. For every 1.0 ml of the stock reagent I, 2.0 ml of distilled water is added to prepare the working reagent.

A second reagent is prepared in the same buffer and pH as used above and 0.1 M creatine phosphate is added. One part of Reagent II is used to 4 parts of Reagent I to yield a 0.02 M concentration of creatine phosphate in the final solution. The final concentration may vary from 0.005 M to 0.05 M. This second reagent (Reagent II) may be divided into appropriate amounts and freeze dried.

TEST METHODS

The test sample may be plasma, serum or whole blood, etc., which is dropped or spotted onto a porous material such as filter paper. The sample is allowed to air dry. It is properly identified and thereafter can be sent by ordinary mail to a centralized test laboratory from any point in the world.

(A) WHOLE BLOOD METHOD (or samples containing indigenous ATP):

The following example in no way limits the volumes, sizes, time or temperature:

1. A ⅛ inch paper punch is used to obtain a ⅛ inch diameter disc from the sample material. The disc is placed in a 6 × 50 mm glass tube.
2. 0.2 ml of the working Reagent I is added.
3. During the first hour, the tube is agitated to facilitate the elution of the sample from the substrate material.
4. The tube is allowed to incubate 20 hours after Reagent I is added to the sample at 20° C. During this time, adenosine triphosphate (ATP) is converted to other products by the excess luciferase with at first an increase and then a decrease in light as the ATP is "consumed."
5. After 20 hours, the intensity of light reaches a base line and 0.05 ml of Reagent II is added and the sample is agitated to ensure uniform mixing.
6. 30 minutes after the addition of Reagent II, the tube is placed in a photometer (such as the CHEMGLOW instrument manufactured by American Instrument Company) and the light intensity is measured.
7. The CPK value is determined from a reference curve constructed from blood with known CPK values as determined by known standard CPK assay methods on plasma portions of the reference blood samples.

(B) SERUM AND PLASMA METHOD (or samples containing no, or negligible amounts of ATP)

The following example in no way limits the volumes, sizes, time or temperature:

1. A ⅛ inch paper punch is used to obtain a ⅛ inch diameter disc from the sample material. The disc is placed in a 6 × 50 mm glass tube.
2. 0.2 ml of working Reagent I and 0.05 ml of Reagent II are added to the tube and agitated to ensure uniform mixing.
3. The tube is allowed to incubate at 22° C for 15 minutes and read in a photometer (such as the aforementioned CHEM-GLOW).
4. The CPK value is determined from a light-intensity reference curve constructed from serum or plasma with known CPK values as determined by known standard CPK assay methods.

While this invention has been described with reference to preferred embodiments and procedures, it is evident that the invention is not limited thereto. Further modifications of the method and products disclosed herein which fall within the scope of the following claims will be immediately evident to those skilled in the art. To the extent that these changes and modifications are within the scope of the appended claims, they are to be considered a part of this invention.

What is claimed is:

1. A method for detecting the presence in an organism of and an increase above a normal level in the concentration of the enzyme creatine phosphokinase in a system in which ATP is either produced or is present, said method comprising
   obtaining a fluid sample from any of a body tissue, body fluid, and an extract of body tissue, of said organism to provide a quantitatively meaningful test fluid,
   depositing said test fluid on a porous carrier,
   drying said fluid on said carrier to provide a dry test specimen stable under normal ambient conditions,
   introducing said test specimen into a test solution including a reagent system reactive with said enzyme contained in said specimen, and
   determining the occurrence of a measurable optical change indicative of the presence of said enzyme in said specimen.

2. The method as set forth in claim 1 for detecting and for determining quantitatively the presence of the enzyme creatine phosphokinase in an organism,
   wherein said reagent system in said test solution includes firefly laatern extract and creatine phosphate, and
   wherein detecting and determining the enzyme comprises sensing and measuring the intensity of any bioluminescent light generated in and emitted from the test solution, and
   quantitatively comparing the light emitted from the test solution with light produced in a reference standard solution, said reference standard solution being pre-calibrated with respect to known creatine phosphokinase concentrations contained therein.

3. The method as set forth in claim 2 and further comprising the step of calculating the creatine phosphokinase present in said test specimen as a function of the light produced in the test solution.

4. The method for diagnosing muscular dystrophy comprising the steps of
   obtaining an extract of body tissue from an organism to provide a quantitatively meaningful test fluid,
   depositing said test fluid on a porous carrier,
   drying said fluid on said carrier to provide a dry test specimen stable under normal ambient conditions
   introducing said test specimen into a test solution including a reagent system reactive with the test specimen, and
   determining the occurrence of a measurable increase in bioluminescent light intensity indicative of the presence of muscular dystrophy in said organism.

5. In the method as set forth in claim 2 a preliminary procedure conducted prior to assaying said test specimen for creatine phosphokinase, said procedure being preliminary to exposure of said test specimen to creatine phosphate and
   comprising the steps of:
   introducing said test specimen into a solution containing firefly lantern extract to which no creatine phosphate has been added,
   allowing any bioluminescent light developed in the solution to be dissipated and, thereafter, adding creatine phosphate to the solution, and measuring the light generated therein as a true measure of the light attributable to creatine phosphokinase contained in said test specimen.

6. The method for screening organisms for the presence of and for monitoring the course of pathological disorders including mental disorders, neuromuscular disorders, consisting essentially of assaying samples of body fluids, extracts and tissues of such organisms for the enzyme creatine phosphokinase in a system in which ATP is either produced or is present to ascertain the presence of a concentration thereof above a normal level, said method comprising, obtaining a fluid sample from any of a body tissue, body fluid, and an extract of body tissue, from said organism to provide a quantitatively meaningful test fluid, depositing said test fluid on a porous carrier, drying said fluid on said carrier to provide a dry test specimen stable under normal ambient conditions, introducing said test specimen into a test solution including a reagent system reactive with said enzyme contained in said specimen, and determining the occurrence of a measurable optical change indicative of the presence of said enzyme in said specimen.

7. The method as set forth in claim 6 for detecting and for determining the serum enzyme creatine phosphokinase present in said test specimen and wherein said reagent system in said test solution includes firefly lantern extract and creatine phosphate, and wherein detecting and determining the enzyme comprises sensing and measuring the intensity of any bioluminescent light generated in and emitted from the test solution, and quantitatively comparing the light emitted from the test solution with light produced in a reference standard solution, said reference standard solution being pre-calibrated with respect to known creatine phosphokinase concentrations contained therein.

8. The method as set forth in claim 7 and further comprising the step of calculating the creatine phosphokinase present in said test specimen as a function of the light produced in the test solution.

9. A method for screening pigs for Porcine Stress Syndrome, comprising measuring the concentration of the enzyme, creatine phosphokinase, present in the tissues of the pigs, above a normal concentrational level of the enzyme indicating that the pigs are affected by the Porcine Stress Syndrome, said method comprising:

obtaining a fluid sample from any of a body tissue, body fluid, and an extract of body tissue from the pig to provide a quantitatively meaningful test fluid, depositing said test fluid on a porous carrier, drying said fluid on said carrier to provide a dry test specimen stable under normal ambient conditions, introducing said test specimen into a test solution containing firefly lantern extract and creatine phosphate, sensing and measuring the intensity of any bioluminescent light generated in and emitted from the test solution, quantitatively comparing the light emitted from the test solution with light produced in a reference standard solution, said reference standard solution being pre-calibrated with respect to known creatine phosphokinase concentrations contained therein, and calculating the creatine phosphokinase present in said test specimen as a function of the light produced in the test solution.

* * * * *

UNITED STATES PATENT OFFICE
CERTIFICATE OF CORRECTION

Patent No. 4,080,265   Dated March 21, 1978

Inventor(s) Alan S. Antonik

It is certified that error appears in the above-identified patent and that said Letters Patent are hereby corrected as shown below:

Title of invention should read -- METHOD FOR THE DETERMINATION OF CREATINE PHOSPHOKINASE ENZYME --.

Claim 2, line 28, "laatern" should read -- lantern --.

Claim 4, line 50, after "conditions" insert -- , --.

Signed and Sealed this

Eighth Day of August 1978

[SEAL]

Attest:

RUTH C. MASON
Attesting Officer

DONALD W. BANNER
Commissioner of Patents and Trademarks